United States Patent
Wu et al.

(10) Patent No.: US 12,385,095 B2
(45) Date of Patent: Aug. 12, 2025

(54) DETECTION OF A TUMOR IN A URINARY ORGAN

(71) Applicants: TAIPEI MEDICAL UNIVERSITY, Taipei (TW); Academia Sinica, Taipei (TW)

(72) Inventors: Yueh-Lin Wu, Taipei (TW); Hsi-Hsien Chen, Taipei (TW); Heng Lin, Taipei (TW); Ji-Yen Cheng, Taipei (TW); Pei-Kuen Wei, Taipei (TW)

(73) Assignees: Taipei Medical University, Taipei (TW); Academia Sinica, Taipei (TW)

( * ) Notice: Subject to any disclaimer, the term of this patent is extended or adjusted under 35 U.S.C. 154(b) by 0 days.

(21) Appl. No.: 16/940,284

(22) Filed: Jul. 27, 2020

(65) Prior Publication Data
US 2021/0025009 A1    Jan. 28, 2021

Related U.S. Application Data

(60) Provisional application No. 62/878,630, filed on Jul. 25, 2019.

(51) Int. Cl.
*C12Q 1/6886* (2018.01)
*C12Q 1/686* (2018.01)

(52) U.S. Cl.
CPC ........... *C12Q 1/6886* (2013.01); *C12Q 1/686* (2013.01); *C12Q 2561/113* (2013.01); *C12Q 2565/628* (2013.01); *C12Q 2565/629* (2013.01); *C12Q 2600/178* (2013.01)

(58) Field of Classification Search
CPC  C12Q 1/6886; C12Q 2600/178; C12Q 1/686; C12Q 2561/113; C12Q 2565/629; C12Q 2600/158; C12Q 2600/118
See application file for complete search history.

(56) References Cited

FOREIGN PATENT DOCUMENTS

KR    20190089552 A    *   7/2019

OTHER PUBLICATIONS

Argyropoulos et al., "Urinary MicroRNA Profiling in the Nephropathy of Type 1 Diabetes," PLoS One, January, vol. 8, No. 1, e54662, pp. 1-13. (Year: 2013).*
Zaporozhchenko et al., "Representation Analysis of miRNA in Urine Microvesicles and Cell-Free Urine in Prostate Diseases," Biochem. Moscow Suppl. Ser. B12, pp. 156-163. (Year: 2018).*
Stuopelyte et al., "Detection of miRNAs in urine of prostate cancer patients," Medicina, pp. 116-124. (Year: 2016).*
Search Report issued in Taiwan Patent Application No. 109125333 on Sep. 13, 2021. (English translation included.).
Armstrong, David A. et al.: "MicroRNA molecular profiling from matched tumor and bio-fluids in bladder cancer," Molecular Cancer, vol. 14, No. 4, Nov. 14, 2015, XP055756961.
European Search Report issued in EP Patent No. 20187962 on Dec. 16, 2020.
Ghorbanmehr, Nassim et al: "miR-21-5p, miR-141-3p, and miR-205-5p levels in urine-promising biomarkers for the identification of prostate and bladder cancer," The prostate, vol. 79, No. 1, Sep. 7, 2018, pp. 88-95, XP055757469.
Osanto, Susanne et al: "Genome-Wide MicroRNA Expression Analysis of Clear Cell Renal Cell Carcinoma by Next Generation Deep Sequencing," PLoS ONE, vol. 7, No. 6, Jun. 20, 2012, p. e38298, XP055757057.
Shiomi, Ei et al: "Analysis of Expression Patterns of MicroRNAs That Are Closely Associated With renal Carcinogenesis," Frontiers in Oncology, vol. 9, May 31, 2019, XP055757562.
Yeung, Wing Kiu et al: "Multiplex detection of urinary miRNA biomarkers by transmission surface plasmon resonance," Analyst, vol. 143, No. 19, Jan. 1, 2018, pp. 4715-4722, JP055756958.

* cited by examiner

*Primary Examiner* — Young J Kim
(74) *Attorney, Agent, or Firm* — Prosyla Group PC

(57) ABSTRACT

The present invention pertains to detection of a tumor in a urinary organ using microRNA(s). MiR-200c-5p, miR-214-3p, miR-21-5p, miR-21-3p, miR-210-3p and/or miR-200b-3p can be used as biomarkers of tumors in a urinary organ to detect a tumor in or predict a prognosis of a tumor in a urinary organ.

6 Claims, 3 Drawing Sheets

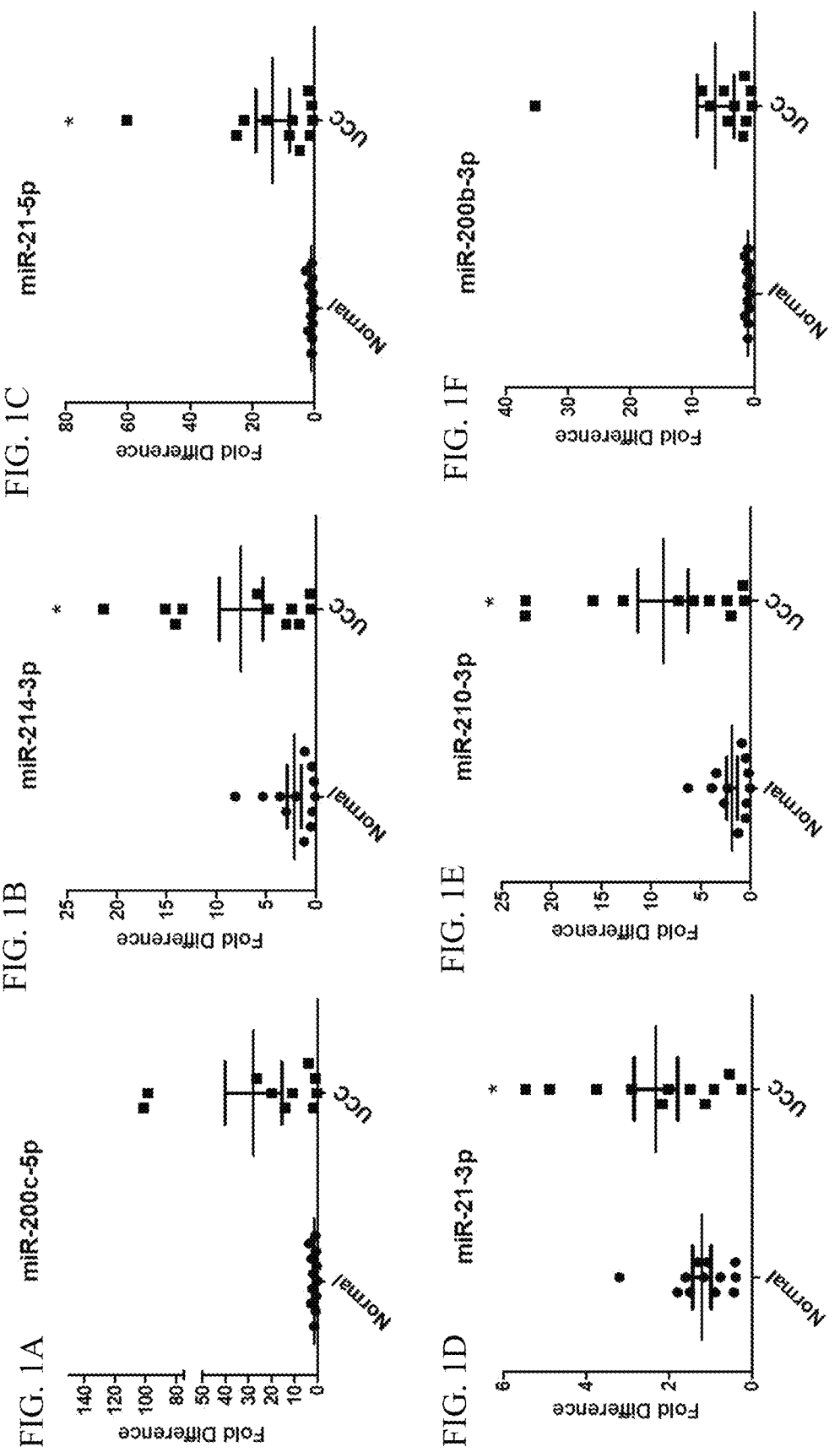

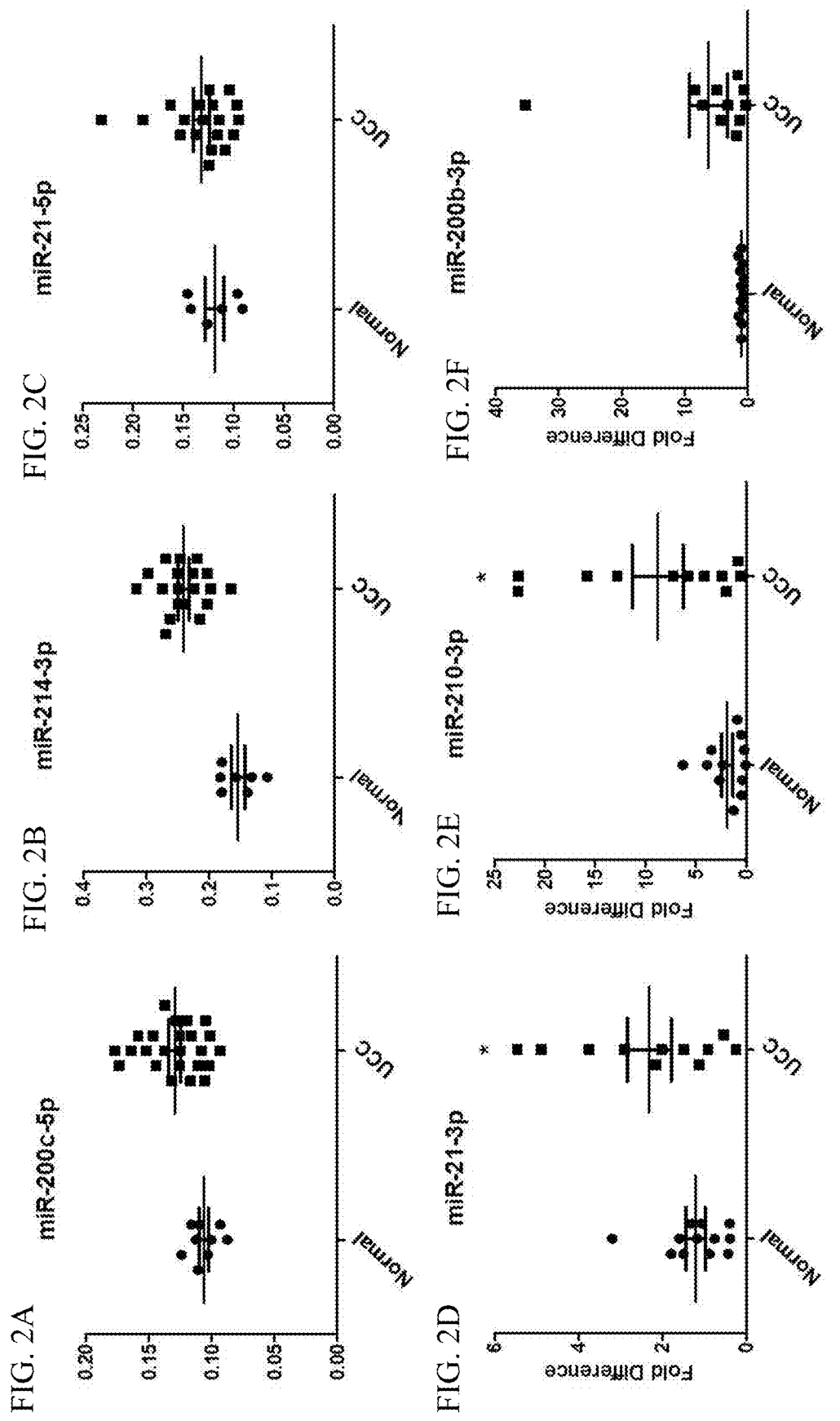

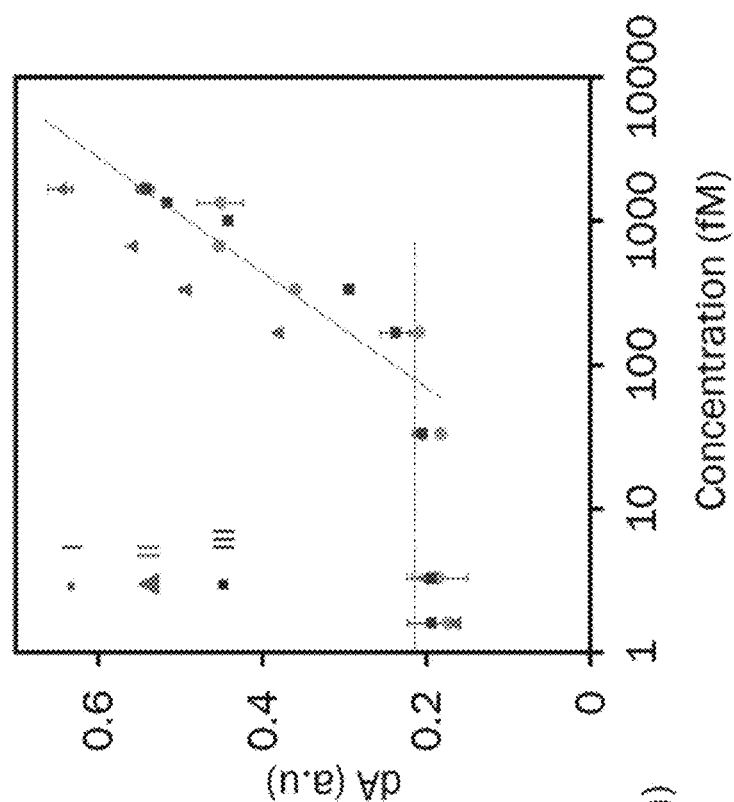
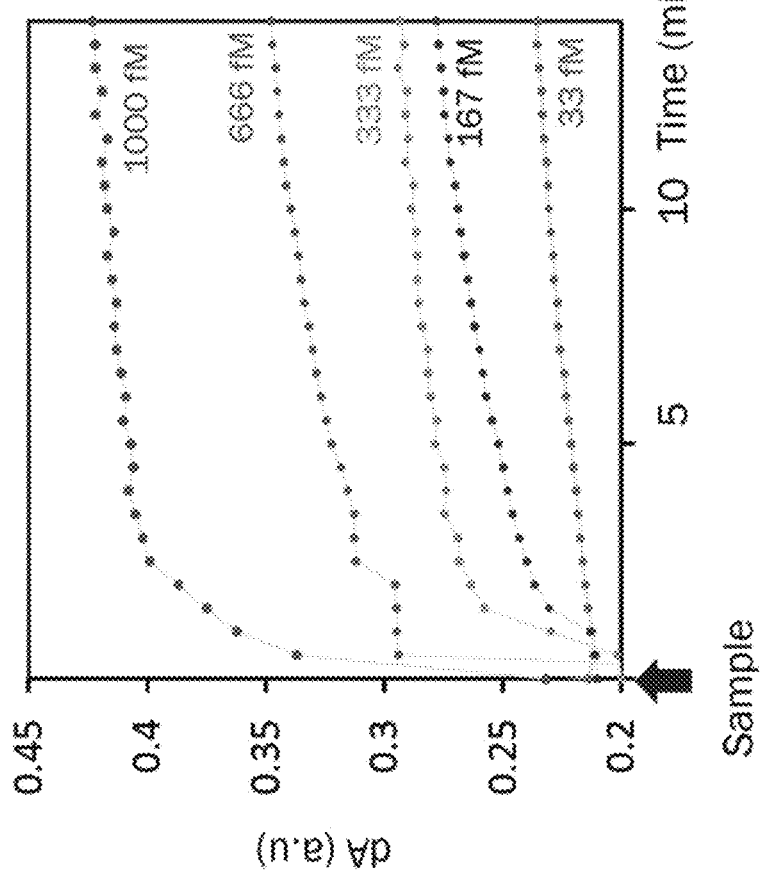
(FIG. 3A)
(FIG. 3B)

DETECTION OF A TUMOR IN A URINARY ORGAN

PRIORITY DATA

This application claims priority to and benefit of Priority Patent Application No. 62/878,630, filed Jul. 25, 2019, the contents of which is incorporated by reference in its entirety.

FIELD OF THE INVENTION

The present disclosure relates to a filed of tumor detection. Particularly, the present disclosure pertains to detection of a tumor in a urinary organ using microRNA(s).

BACKGROUND OF THE INVENTION

Urothelial carcinoma (UCC), also transitional cell carcinoma (TCC), is a type of cancer that typically occurs in the urinary system. It characterized the most common form of bladder cancer and cancer of the ureter, urethra, and urachus. However, urothelial tumors of the renal pelvis and ureters (upper urinary tract) are relatively less. The bladder is the most common site of UCC, 50 times more common than UCC of the renal pelvis, and 100 times more common than UCC of the ureter. Bladder UCC is the most common tumor of the entire urinary tract.

In 2017, an estimated 17000 deaths are caused by bladder cancer (BCa) in the United States. From the National Cancer Institute's SEER database, the non-invasive bladder cancer is almost curable disease as the 5-year survival rate of 90-95%, but the very poor outcome for metastatic disease as the 5-year survival rate of ~12%. The overall prognosis of the 5-year survival rate in all stages together is still quite poor for only about 45%. Therefore, the early detection is the majority of the management of urothelial carcinoma. The full range of conventional diagnostic methods, including cystoscopy, urine cytology, excretory urography, and ultrasonography are used for diagnosis and monitoring of UCC. Some are uncomfortable, time-consuming, and invasive; they are also insufficient regarding their sensitivity and specificity.

US 20070054287A1 provides methods for detecting biological conditions such as cancer by using micro RNAs as tissue-specific biomarkers. US 20110312516A1 relates to the identification and use of miRNAs to detect, diagnose and/or predict the course, progression or therapy responsiveness of bladder cancer.

Currently, the standard of monitoring of UCC requires repeated cystoscopy every 3 months, then every 6 months for the next 2 years and annually for another 10 years. Although cystoscopy is reportedly 90% sensitive, testing is highly invasive; in some cases, it does not provide a definite diagnosis, particularly in cases where the size of the tumor is too small or in the case of carcinoma in situ. Furthermore, urine cytology is currently the standard of noninvasive procedure for early diagnosis and follow-up; unfortunately, the use is limited by its low sensitivity.

SUMMARY OF THE INVENTION

The present disclosure relates to the finding that miR-200c-5p, miR-214-3p, miR-21-5p, miR-21-3p, miR-210-3p and/or miR-200b-3p can independently or in combination be used as biomarkers of tumors in a urinary organ. The expression of biomarker(s) described herein can be indicative of a tumor or prognosis of a tumor in an urinary organ.

In one aspect, the present disclosure provides a method of detecting or diagnosing if a subject has, or is at risk of developing a tumor in a urinary organ, a tumor in a urinary organ of a subject, or assessing a prognosis of a tumor in a urinary organ, comprising a) measuring the expression level of one or more micro RNAs (miRNAs) selected from the group consisting of: miR-200c-5p, miR-214-3p, miR-21-5p, miR-21-3p, miR-210-3p and miR-200b-3p in a biological sample taken from the subject, and b) comparing the measured level(s) of the one or more miRNAs against a reference expression level(s) of the same one or more miRNAs, wherein an increased expression level(s) of the one or more miRNAs compared to the reference expression level(s) of the same one or more miRNAs is indicative that the subject having, or being at risk of developing a tumor in a urinary organ or having a poor prognosis for the survival of the subject.

In one embodiment, the biological sample is a urine sample.

In one embodiment, the miRNAs are used in combination.

In one embodiment, the miRNAs comprise at least the two miRNAs selected from the groups consisting of: miR-200c-5p, miR-214-3p, miR-21-5p, miR-21-3p, miR-210-3p and miR-200b-3p.

In some embodiments, the miRNAs comprise at least miR-21-3p or miR-21-5p. In some embodiments, the miRNAs comprise a combination selected from the group consisting of miR-21-3p and miR-210-3p; miR-21-3p and miR-214-3p; miR-214-3p and miR-210-3p; miR-214-3p, miR-21-3p and miR-210-3p; miR-21-3p and miR-21-5p; miR-21-5p, miR-21-3p, miR-210-3p; and miR-214-3p, miR-21-5p and miR-210-3p.

In some embodiments, the tumor in a urinary organ is urothelial carcinoma (UCC) or renal cell carcinoma (RCC).

In one embodiment, the detection or diagnosis of a tumor in a urinary organ is early detection or diagnosis.

In one embodiment, the tumor in a urinary organ is metastatic.

In one embodiment, the subject is human.

In some embodiments, the presence or level(s) of one or more specific micro RNAs are determined by a real time PCR or surface plasmon resonance (SPR). In a further embodiment, the surface plasmon resonance is nano-SPR (surface plasmon resonance). In some embodiments, the expression levels of miR-200c-5p, miR-214-3p, miR-21-5p, miR-21-3p, miR-210-3p and miR-200b-3p in a subject are about 30+/−10 folds, about 7.5+/−1.5 folds, about 18+/−2 folds, about 2.5+/−0.5 folds, about 9+/−2 folds and about 7.5+/−2 folds higher than the reference expression level, respectively, as determined by real time PCR. In some embodiments, the expression levels of miR-200c-5p, miR-214-3p, miR-21-5p, miR-21-3p, miR-210-3p and miR-200b-3p in a subject are about 1.3+/−0.05 folds, about 1.67+/−0.01 folds, about 1.08+/−0.04 folds, about 2.5+/−0.01 folds, about 4+/−0.02 folds and about 7+/−0.02 folds higher than the reference expression level, respectively, as determined by SPR.

In another aspect, the present disclosure provides a kit for measuring the expression level of one or more miRNA, comprising one or more sequence complementary to one or more of miRNAs selected from the group consisting of: miR-200c-5p, miR-214-3p, miR-21-5p, miR-21-3p, miR-210-3p and miR-200b-3p. In one embodiment, the sequence is probe, primer or cDNA.

In another aspect, the present disclosure provides a system for measuring the expression level of one or more miRNA, comprising a) microfluidic chip containing one or more sequence complementary to one or more of miRNAs selected from the group consisting of: miR-200c-5p, miR-214-3p, miR-21-5p, miR-21-3p, miR-210-3p and miR-200b-3p and b) a surface plasmon resonance sensor device.

BRIEF DESCRIPTION OF THE DRAWINGS

FIGS. 1A to 1F show the expression level of each of miR-200c-5p (FIG. 1A), miR-214-3p (FIG. 1), miR-21-5p (FIG. 1C), miR-21-3p (FIG. 1D), miR-210-3p (FIG. 1E) and miR-200b-3p (FIG. 1F) in urine samples of UCC patients in real-time PCR assay.

FIGS. 2A to 2F show the expression level of each of miR-200c-5p (FIG. 2A), miR-214-3p (FIG. 2B), miR-21-5p (FIG. 2C), miR-21-3p (FIG. 2D), miR-210-3p (FIG. 2E) and miR-200b-3p (FIG. 2F) in urine samples of UCC patients in SPR assay.

FIGS. 3A and 3B show that the signals of three miRNAs (miR-214-3p, miR-21-3p and miR-210-3p) in urine samples (FIG. 3A) and diluted samples (FIG. 3B) in SPR microfluidic chips can be simultaneously measured in SPR assay.

DETAILED DESCRIPTION OF THE INVENTION

The definitions of certain terms as used in this specification are provided below. Unless defined otherwise, all technical and scientific terms used herein generally have the same meaning as commonly understood by one of ordinary skill in the art to which this present technology belongs.

The singular forms "a," "an" and "the" include plural reference unless the context clearly dictates otherwise.

The term "and/or" wherever used herein includes the meaning of "and", "or" and "all or any other combination of the elements connected by said term."

As used herein, the terms "subject," "individual," or "patient" can be an individual organism, a vertebrate, a mammal, or a human.

As used herein, the term "biomarker" may be defined as a biological molecule found in a biological sample that is an indicator of a normal or abnormal process, or of a condition or disease.

As used herein the term "metastatic" (and all other forms and tenses, including, for example, metastasis, meta stasize, etc.) when used alone or in conjunction with cancer refers to the spread of a cancer from one part of the body to another, unless otherwise indicated by the use or context. Typically, a tumor formed by cells that have spread is called a "metastatic tumor" or a "metastasis." The metastatic tumor contains cells that are like those in the original (primary) tumor.

As used herein, the term "biological sample" means any fluid or other material derived from the body of a normal or diseased subject, such as tissue, blood, serum, plasma, lymph, urine, saliva, tears, cerebrospinal fluid, amniotic fluid, bile, ascites fluid, pus, and the like. Methods of obtaining biological samples are well known in the art. Extraction of RNA, e.g., miRNA, from a biological sample may be performed using well-known methods in the art.

As used herein, the terms "microRNA", "miRNA" and "miR" are used synonymously to refer to an about 18-25 nucleotide (nt) long, non-coding RNAs derived from endogenous genes. "MicroRNA" (miRNA) includes primary miRNA transcripts (pri-miRNA) or other mRNA transcripts that code for mature miRNA (e.g., miRNA processed from introns excised from mRNA transcripts), precursor miRNAs (pre-miRNA), mature single stranded miRNAs, and variants thereof, which may be naturally occurring. The term "miRNA" includes human and miRNA from other mammals. In some instances, the term "miRNA" also includes primary miRNA transcripts and duplex miRNAs. Unless otherwise noted, when used herein, the name of a specific miRNA refers to the mature miRNA of a precursor miRNA. Some single primary miRNA transcripts may contain more than one precursor/mature miRNA. Some mature miRNA may be derived from more than one precursor miRNA.

As used herein, the term "reference expression profile" or other calculated level of an miR molecule or other biomarker of a marker can be any amount or a range of amounts to be compared against a test amount of a marker.

As used herein, the term "expression" denotes the product of an RNA produced through transcription of a gene or the production of the protein product encoded by a nucleotide sequence.

As used herein, the term "increased expression" or "increasing expression," indicate that expression of a particular gene sequence in a cell, tissue, organ, or organism has been increased relative to an untreated or control cell, tissue, organ, or organism.

As used herein, the terms "diagnosing" and "diagnosis" as used herein refer to methods by which the skilled artisan can estimate and even determine whether or not a subject is suffering from a given disease or condition. The skilled artisan often makes a diagnosis on the basis of one or more diagnostic indicators, such as for example a biomarker (e.g., an miRNA expression level), the amount (including presence or absence) of which is indicative of the presence, severity, or absence of the condition.

As used herein, the terms "prognose," "prognosing," "prognosis," and variations thereof refer to the course of a disease or condition in an individual who has the disease or condition (e.g., patient survival), and such terms encompass the evaluation of disease response after the administration of a treatment or therapy to the individual.

Novel strategies for early diagnosis of patients with a tumor in a urinary organ are urgently needed. The present disclosure surprisingly found that one or more micro RNAs (miRNAs) selected from the group consisting of: miR-200c-5p, miR-214-3p, miR-21-5p, miR-21-3p, miR-210-3p and miR-200b-3p in a biological sample can be used as biomarker(s) for detecting or diagnosing a tumor in urinary organs or assessing a prognosis of a tumor in a urinary organ. The use of miRNA expression levels as biomarkers in a biological sample improves the diagnostic tools for tumors in urinary organ. Particularly, the biological sample is urine sample.

MicroRNAs (miRNA) are single-stranded RNA molecules of about 19-25 nucleotides in length, which regulate gene expression. miRNAs are either expressed from non-protein-coding transcripts or mostly expressed from protein coding transcripts. They are processed from primary transcripts known as pri-miRNA to shorter stem-loop structures called pre-miRNA and finally to functional mature miRNA. Mature miRNA molecules are partially complementary to one or more messenger RNA (mRNA) molecules, and their main function is to inhibit gene expression. This may occur by preventing mRNA translation or increasing mRNA turnover/degradation.

The miRNA biomarkers may be applied ex vivo to a urine sample obtained from a subject, in order to facilitate an early and accurate diagnosis of and/or prognosis for said individual. The use of the miRNA(s) described herein can improve the diagnosis of a tumor in a urinary organ and allow for an earlier diagnosis. Early diagnosis of a malignant condition of the urinary organ is urgently needed in order to present cancer patient to a therapy at a less advanced stage. Particularly, the tumor in a urinary organ is urothelial carcinoma (UCC) or renal cell carcinoma (RCC).

Accordingly, provided herein are methods and systems for detecting or diagnosing if an individual has, or is at risk of developing a tumor in a urinary organ, a tumor in a urinary organ of a subject, or assessing a prognosis of a tumor in a urinary organ, comprising the steps of measuring the expression level of one or more micro RNAs (miRNAs) selected from the group consisting of: miR-200c-5p, miR-214-3p, miR-21-5p, miR-21-3p, miR-210-3p and miR-200b-3p in a biological sample taken from the subject, and determining whether the subject has, or is at risk of developing a tumor in a urinary organ or has a poor prognosis for the survival of the subject.

It is contemplated that the expression level of at least one of said miRNAs in one embodiment is measured in a sample from a subject, and said miRNA expression level is then associated with a prognosis.

In one embodiment, the miRNAs are used in combination; i.e. the expression level of at least the two miRNAs selected from the groups consisting of: miR-200c-5p, miR-214-3p, miR-21-5p, miR-21-3p, miR-210-3p and miR-200b-3p. In a further embodiment, the miRNAs comprise miR-21-5p and miR-21-3p.

Before performing the methods according to the present inventions, if necessary, RNA may be extracted from biological samples and purified using methods known in the art. Many methods are known for isolating total RNA, or to specifically extract small RNAs, including miRNAs. The RNA may be extracted using commercially-available kits (e.g., Perfect RNA Total RNA Isolation Kit, Five Prime-Three Prime, Inc.; mirVana® kits, Ambion, Inc.).

Any method of measuring or quantitating the amount of miRNA in a biological sample can be used. Preferred methods are reliable, sensitive and specific for a particular miRNA used as a biomarker in aspects of the present invention. Examples of the methods include, but are not limited to, PCR methods, northern blot analysis, affinity matrices and surface plasmon resonance. Methods such as differential display, RNAase protection assays and Northern or Southern blots may be used to quantify miRNA in a biological sample, or indirectly quantify miRNA in a biological sample through amplification and detection of cDNA oligonucleotides (completely or partially) complementary or (completely or partially) identical to the miRNA biomarker. A qRT-PCR method offers more sensitive and less labor-intensive quantification of miRNA in samples. MiRNA may or may not be amplified by techniques such as polymerase chain reaction (PCR) prior to measurement, or the quantity of miRNA may be directly or indirectly measured during amplification. Quantitative assessments such as real-time quantitative PCR (qRT-PCR) assay are simple, sensitive, reproducible, and cost-effective; hence they are suitable to use as a diagnostic tool.

In one embodiment, the level(s) of one or more specific miRNAs are determined by a real time PCR. In some embodiments, the methods of the present inventions comprise amplifying the miRNAs. Many methods exist for amplifying miRNA nucleic acid sequences such as mature miRNAs, primary miRNAs and precursor miRNAs. Suitable nucleic acid polymerization and amplification techniques include reverse transcription (RT), polymerase chain reaction (PCR), real-time PCR (quantitative PCR (q-PCR)), nucleic acid sequence-base amplification (NASBA), ligase chain reaction, multiplex ligatable probe amplification, invader technology (Third Wave), rolling circle amplification, in vitro transcription (IVT), strand displacement amplification, transcription-mediated amplification (TMA), RNA (Eberwine) amplification, and other methods that are known to persons skilled in the art. In certain embodiments, more than one amplification method is used, such as reverse transcription followed by real time quantitative PCR (qRT-PCR).

In one embodiment, the level(s) of one or more specific miRNAs are determined by surface plasmon resonance (SPR) in combination with a microfluidic chip. The present disclose uses the new developed miRNAs described herein, microfluidics and nano-SPR (surface plasmon resonance) technology to develop a portable urine detector that can detect microRNA (miR) in the urine of patients. Accordingly, the present disclosure provides a portable SPR system for detecting biomarkers in urine sample.

In one embodiment, the expression level of one or more miRNAs is determined by the northern blot technique. A northern blot is a method used to check for the presence of a RNA sequence in a sample. Northern blotting combines denaturing agarose gel or polyacrylamide gel electrophoresis for size separation of RNA with methods to transfer the size-separated RNA to a filter membrane for probe hybridization. The hybridization probe may be made from DNA or RNA.

In some aspects, probes and or primers to detect amplified or unamplified miRNAs or completely or partially complementary or completely or partially identical cDNAs may be oligonucleotides having sequences completely or partially complementary or completely or partially identical to the amplified miRNA or cDNA. In one embodiment, the probe and/or primer is a cDNA. In one embodiment, the probe and or primer is labeled to aid in the detection of the amplified or unamplified miRNAs or completely or partially complementary or completely or partially identical cDNAs.

Having now generally described the invention, the same will be more readily understood through reference to the following examples, which are provided by way of illustration, and are not intended to be limiting of the present invention, unless specified.

EXAMPLE

Urine Samples

A total of 66 human urine samples were obtained in Taipei Medical University Hospital (Taipei, Taiwan) from March 2019 to April 2019. This research project was approved by the Taipei Medical University Joint Institutional Review Board (TMU-JIRB N201902019) and consents were obtained from 25 healthy volunteers, 4 lung cancer patients and 36 UCC patients before tissue biopsy or surgery accordance with the approved protocols and guidelines. In this work, samples were collected from UCC patients, defined as those undergone the 'gold standard' of cystoscopy and samples had undergone histopathological analysis and clinical follow-ups. Urine samples were collected and centrifuged at 16,000 rpm for 20 min and the supernatant was aliquoted into Eppendorf tubes and stored at −80° C. until use. The relevant information of these participants is listed in Table 1.

TABLE 1

Baseline clinical and pathological features of patients with UCC

| Characterisitics | | UCCs (n = 36) | Lung Cancer (n = 4) | Controls (n = 25) |
|---|---|---|---|---|
| Mean Age ± SD | | 63.6 ± 7.7 | 63.0 ± 4.5 | 58.7 ± 3.2 |
| Gender | Female | 18(50%) | 2(50%) | 13(52%) |
| | Male | 18(50%) | 2(50%) | 12(48%) |
| Hematuria | | 31(86.1%) | — | — |
| UCC | High Grade | 27 | — | 0 |
| stage | Low Grade | 9 | — | 0 |
| Comorbid | CKD | 4 | — | — |
| | CVD | 13 | — | — |
| Liver Disease | | 1 | — | 0 |
| Lung Disease | | 2 | 2 | 0 |

Selection of Putative Target miRNA.

A total of 9miRNAs from four different miRNA families (miR-21, miR-214, miR-210, miR-200) were selected for current study.

RNA Isolation

The human urine RNA was extracted using the QiAMP circulating nucleic acid kit (Qiagen, Germantown, MD). RNA isolation was performed according to the manufacturer's instructions.

Quantitative PCR and Reverse Transcription PCR

The ABI Step One Plus Real-Time PCR System (ABI) (Thermo Fisher Scientific, Waltham, MA) was used for quantitative PCR (q-PCR) analysis. For the detection of miRNAs (miR-21-5p, miR-21-3p, miR-200c-3p, miR-210-3p, miR-214-5p, miR-214-3p, miR-200b-3p, miR-200c-5p) expression, stem-loop q-PCR was carried out using the TaqMan miRNA Assays with TaqMan® Universal Master Mix II according to standard procedure (Life Technologies, CA, USA). Q-PCR was performed using the TaqMan 2× universal master mix and 20×TaqMan miRNA assay (primers & probe). All samples were run in duplicate and the resulting Ct values averaged. Relative expression was evaluated by the comparative threshold cycle method. The expression of miRNAs was normalized to the expression of Cel-miR-39, which is commonly used as a reference gene in miRNA quantification (Poel, D., T. E. Buffart, J. Oosterling-Jansen, H. M. W. Verheul and J. Voortman, *Evaluation of several methodological challenges in circulating miRNA qPCR studies in patients with head and neck cancer. Experimental & Molecular Medicine*, 2018. 50(3):p. e454-e454.)

t-SPR Working Principle and Double Hybridization Measurement

All transmission SPR measurement in this work were performed using a custom-built platform. A stabilized collimated light shine onto the sensor and the transmitted light was collected by the miniaturized spectrometer. The XY stage and the spectrometer are controlled by the in-house build LabVIEW software. The immobilized CG nano-slit integrated microfluidic chips were mounted onto the sample holder on the XY stage. A total of 4 integrated microfluidic chip can be analyzed simultaneously.

The disposable PMMA (Poly(methyl methacrylate) microfluidic chip is integrated with functionalised capped gold nano-slit (CG nano-slit) sensor. Independent sensing regions dedicated to each miRNA is arranged on the CG nano-slit. Functionalised approach is described below. This work relies upon the double hybridisation method, where the monitoring probe immobilised onto the CG nano-slit surface is a 3'thiol modified 22-mer oligonucleotide (poly(dT)11 spacer and 11 complimentary bases) meanwhile the capturing probe immobilised onto the commercially available AuNP is a 5'thiol modified 22-mer oligonucleotide (poly(dT)11 spacer and 11 complimentary bases). In brief, 11-mer of the urinary target miRNA binds to the capturing probe on the AuNP forming the working solution. When the working solution is introduced into the microfluidic device, the functionalized AuNP-target (f(AuNP)-target) complex binds onto the sensor surface due to specific complementary pairing to the other half of the target miRNA to the monitoring probe, completing the double hybridization process.

In terms of the optical set-up, t-SPR measures the RI changes at the surface of the metallic layers. Owning to the nano-slit structure, the interference of the cavity mode and the surface plasmon resonant mode produces an asymmetric Fano resonance peak. The complementary hybridisation approach binds the f(AuNP)-target close to the sensor surface, and the interference of plasmon resonance between the AuNP and gold nano-slit sensor results in an amplification of signal change.

Using a syringe pump, the PBS buffer was withdrawn from the reservoir at a rate of 240 µl/min for 10 mins to fill the microfluidic chip, the respective spectra is recorded per minute as the system baseline reference. Aliquot containing 60 µl of urine was thawed at 4° C., mixed with 6 µl of RIPA Lysis reagent (ThermoScientific Cat #89900) and vortex for 30 s. Commercially available AuNP (Nanocomposix, CA d=7 nm, $1.44 \times 10^{13}$ particles/mL) functionalised with the capturing probe were prepared and for multiplex detection purpose, 90 µl of the corresponding functionalized AuNP is added to the working solution per target miRNA. Also, 20×SSC (30 µl) is added to the working solution to enhance hybridization and vortexed for 30 seconds and subsequently added to the inlet reservoir of the microfluidic chip without additional incubation time. The urine sample containing functionalized AuNP was carried over the sensor surface at 240 µl/hr for 1.5 hours and the t-SPR system that is controlled by an in-house designed program to record one spectral measurement per minute per sensing region. The spectrum recorded was processed into a transmission spectrum and the change in the Fano peak spectral area over time was calculated (dA), using the method described in the previous work (Yeung, W. K, H. Y. Chen, J. J. Sun, T. H. Hsieh, M. Z. Mousavi, H. H. Chen, K. L. Lee, H. Lin, P. K. Wei and J. Y. Cheng, *Multiplex detection of urinary miRNA biomarkers by transmission surface plasmon resonance. Analyst*, 2018. 143(19): p. 4715-4722.) In brief, it integrates the area under the spectra ranges from 670-690 nm, and compares the area change with that obtained when t=0. The t-SPR measurement was conducted under single blind test.

Example 1 Real-Time PCR Assay of miRNAs in Urine Sample of UCC Patients

As shown in FIG. 1, the expression level of each of miR-200c-5p, miR-214-3p, miR-21-5p, miR-21-3p, miR-210-3p and miR-200b-3p in urine samples of UCC patients is higher than that of subjects without UCC.

Example 2 SPR Assay of miRNAs in Urine Sample of UCC Patients

Urine sampling from UCC patients and healthy controls has been obtained to detect miRNAs expression by SPR assay. As shown in FIG. 2, the expression level of each of miR-200c-5p, miR-214-3p, miR-21-5p, miR-21-3p, miR-210-3p and miR-200b-3p in urine samples of UCC patients is higher than that of subjects without UCC.

Example 3 Automated SPR Measurement System for Measuring miRNAs in Urine Sample of UCC Patients The automated SPR measurement system uses transmissive surface plasmon resonance in combination with a position automatic control and a microfluidic chip to measure and analyze spectrum change caused by binding of target miRNA(s) to the complementary sequences thereof (Methods Mol Biol. 2009; 503:37-47). A stabilized light shines collimated light onto the sensor surface and captured by the miniaturized spectrometer. The X-Y stage of array-based spectral SPR biosensor and the spectrometers are controlled by the in-build LabVIEW software. The SPR microfluidic chips were mounted onto the sample holder on the programmable X and Y stages. The system is portable and can measure miRNA in a very low concentration (33 fM). FIG. 3 shows that the signals of three miRNAs (miR-214-3p, miR-21-3p and miR-210-3p) in a urine sample can be simultaneously measured and the limitation of detection is 33 fM. No PCR is needed. Real-time monitoring of the kinetic binding of target sequence in the microfluidic chip and the calibration curve obtained for various concentrations of three different targets: I, II and III (miR-214-3p, miR-21-3p and miR-210-3p, respectively), spiked in urine from healthy participants. The dA is the measured signal representing target binding. The error bar represents the standard error of the mean.

What is claimed is:

1. A method for measuring the expression level of micro RNA (miRNA), comprising a) taking a urine sample from a subject; b) measuring the expression level of miR-214-3p in the urine sample taken from the subject; and c) measuring the expression level of miRNAs comprising miR-21-5p and miR-21-3p in the urine sample taken from the subject.

2. The method of claim 1, wherein in c), the miRNAs further comprise miR-210-3p.

3. The method of claim 1, wherein the subject is human.

4. The method of claim 1, wherein b), the expression level of miR-214-3p in the urine sample taken from the subject is measured by a real-time PCR or surface plasmon resonance (SPR).

5. The method of claim 4, wherein the SPR is nano-SPR.

6. The method of claim 1, further wherein in c), the expression level of the miRNAs in the urine sample taken from the subject is measured by a real-time PCR or SPR.

* * * * *